(12) United States Patent
Adams (10) Patent No.: US 9,522,012 B2
(45) Date of Patent: *Dec. 20, 2016

(54) SHOCKWAVE CATHETER SYSTEM WITH ENERGY CONTROL (71) Applicant: SHOCKWAVE MEDICAL, INC., Fremont, CA (US)

(72) Inventor: John M. Adams, Snohomish, WA (US)

(73) Assignee: SHOCKWAVE MEDICAL, INC., Fremont, CA (US)

(*) Notice: Subject to any disclaimer, the term of this patent is extended or adjusted under 35 U.S.C. 154(b) by 317 days.

This patent is subject to a terminal disclaimer.

(21) Appl. No.: 14/218,858

(22) Filed: Mar. 18, 2014

(65) Prior Publication Data
US 2014/0288570 A1 Sep. 25, 2014

Related U.S. Application Data (63) Continuation-in-part of application No. 13/615,107, filed on Sep. 13, 2012.

(51) Int. Cl.
A61B 17/22 (2006.01)

(52) U.S. Cl.
CPC ........... A61B 17/22022 (2013.01); A61B 2017/22025 (2013.01); A61B 2017/22062 (2013.01); A61B 2017/22081 (2013.01)

(58) Field of Classification Search
CPC ........... A61B 17/22022; A61B 2017/22025; A61B 2017/22062; A61B 2017/22081
See application file for complete search history.

(56) References Cited

U.S. PATENT DOCUMENTS 3,413,976 A 12/1968 Roze
3,785,382 A 1/1974 Schmidt et al.
(Continued)

FOREIGN PATENT DOCUMENTS

DE 3038445 A1 5/1982
EP 0442199 A2 8/1991
(Continued)

OTHER PUBLICATIONS

Non Final Office Action received for U.S. Appl. No. 12/482,995, mailed on Aug. 13, 2014, 10 pages.
(Continued)

Primary Examiner — Gregory Anderson
Assistant Examiner — Son Dang
(74) Attorney, Agent, or Firm — Morrison & Foerster LLP (57) ABSTRACT A system includes a catheter including an elongated carrier, a balloon about the carrier in sealed relation thereto, the balloon being arranged to receive a fluid therein that inflates the balloon, and first and second electrodes within the balloon arranged to carry a voltage there-across including an initial high electrical voltage at an initial low current. The initial high electrical voltage causes an electrical arc to form across the first and second electrodes within the balloon. The electrical arc causes a gas bubble within the liquid, a high current to flow through the first and second electrodes, a decrease in the initial high electrical voltage, and a mechanical shock wave within the balloon. The system further includes a power source that provides the first and second electrodes with a drive voltage that creates the initial high electrical voltage at the initial current and that terminates the drive voltage in response to the decrease in the initial high electrical voltage.

27 Claims, 7 Drawing Sheets

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,900,303 A | 2/1990 | Lemelson |
| 5,009,232 A | 4/1991 | Hassler et al. |
| 5,057,103 A | 10/1991 | Davis |
| 5,057,106 A | 10/1991 | Kasevich et al. |
| 5,078,717 A | 1/1992 | Parins et al. |
| 5,103,804 A | 4/1992 | Abele et al. |
| 5,152,767 A | 10/1992 | Sypal et al. |
| 5,152,768 A | 10/1992 | Bhatta |
| 5,176,675 A | 1/1993 | Watson et al. |
| 5,245,988 A | 9/1993 | Einars et al. |
| 5,246,447 A | 9/1993 | Rosen et al. |
| 5,281,231 A | 1/1994 | Rosen et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,931,805 A | 8/1999 | Brisken |
| 6,007,530 A | 12/1999 | Doernhoefer et al. |
| 6,033,371 A | 3/2000 | Torre et al. |
| 6,083,232 A | 7/2000 | Cox |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,569,032 B2 | 8/2009 | Naimark et al. |
| 8,556,813 B2 | 10/2013 | Cioanta et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 9,011,463 B2 | 4/2015 | Adams et al. |
| 9,333,000 B2 | 5/2016 | Hakala et al. |
| 2001/0044596 A1 | 11/2001 | Jaafar |
| 2002/0045890 A1 | 4/2002 | Celliers et al. |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0113722 A1 | 5/2005 | Schultheiss |
| 2005/0228372 A1 | 10/2005 | Truckai et al. |
| 2005/0251131 A1 | 11/2005 | Lesh |
| 2006/0004286 A1 | 1/2006 | Chang et al. |
| 2006/0184076 A1 | 8/2006 | Gill et al. |
| 2006/0190022 A1 | 8/2006 | Beyar et al. |
| 2007/0088380 A1 | 4/2007 | Hirszowicz et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0282301 A1 | 12/2007 | Segalescu et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0150874 A1 | 6/2013 | Kassab |
| 2014/0046229 A1 | 2/2014 | Hawkins et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0243820 A1 | 8/2014 | Adams et al. |
| 2014/0243847 A1 | 8/2014 | Hakala et al. |
| 2015/0073430 A1 | 3/2015 | Hakala et al. |
| 2015/0238208 A1 | 8/2015 | Adams et al. |

FOREIGN PATENT DOCUMENTS

| | | |
|---|---|---|
| EP | 0571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| JP | 2007-532182 A | 11/2007 |
| WO | 96/24297 A1 | 8/1996 |
| WO | 2004/069072 A2 | 8/2004 |
| WO | 2005/099594 A1 | 10/2005 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/143468 A2 | 11/2011 |
| WO | 2013/059735 A1 | 4/2013 |

OTHER PUBLICATIONS

Advisory Action Received for U.S. Appl. No. 12/581,295, mailed on Jul. 3, 2014, 3 pages.

Final Office Action received for U.S. Appl. No. 12/581,295, mailed on Jun. 5, 2014, 14 pages.

Final Office Action received for U.S. Appl. No. 13/049,199 mailed on Aug. 11, 2014, 8 pages.

(56) References Cited

OTHER PUBLICATIONS

Notice of Allowance received for U.S. Appl. No. 13/831,543, mailed on Oct. 8, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Notice of Acceptance Received for Australian Patent Application No. 2009257368, mailed on Aug. 28, 2014, 2 pages.
Office Action received for Australian Patent Application No. 2009257368, issued on Apr. 28, 2014, 4 pages.
Office Action Received for Japanese Patent Application No. 2011-513694, mailed on Jun. 10, 2014, 2 pages of Official Copy only (See Communication under 37 CFR § 1.98(a) (3)).
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep, vol. 14, 2012, pp. 567-572.
Kodama et al., "Shock Wave-Mediated Molecular Delivery Into Cells", Biochimica et Biophysica Acta, vol. 1542, 2002, pp. 186-194.
Lauer et al., "Shock Wave Permeabilization as a New Gene Transfer Method", Gene Therapy, vol. 4, 1997, pp. 710-715.
Doug Hakala, "Unpublished U.S. Appl. No. 14/515,130, filed Oct. 15, 2014, titled "Low Profile Electrodes for an Angioplasty Shock Wave Catheter"".
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Written Opinon received for PCT Patent Application No. PCT/US2009/047070, mailed on Jan. 19, 2010, 5 pages.
International Preliminary Report on Patentability received for PCT Patent Application No. PCT/US2009/047070, mailed on Dec. 23, 2010, 7 pages.
Non-Final Office Action received for U.S. Appl. No. 12/581,295, mailed on Mar. 10, 2014, 11 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Adams et al., Unpublished U.S. Appl. No. 14/271,342, filed May 6, 2014, titled "Shock Wave Balloon Catheter with Multiple Shock Wave Sources", 21 pages.
Hakala et al., Unpublished U.S. Appl. No. 14/271,276, filed May 6, 2014, titled "Shockwave Catheter System with Energy Control", 20 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Notice of Allowance received for U.S. Appl. No. 12/482,995, mailed on Dec. 24, 2014, 6 pages.
Non-Final Office Action received for U.S. Appl. No. 12/581,295, mailed on Jan. 15, 2015, 14 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Advisory Action Received for U.S. Appl. No. 13/049,199, mailed on Jun. 7, 2012, 3 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Final Office Action Received for U.S. Appl. No. 13/267,383, mailed on May 28, 2015, 12 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Notice of Allowance received for U.S. Appl No. 13/465,264, mailed on May 8, 2015, 7 pages.
Final Office Action received for U.S. Appl. No. 13/615,107 mailed on Sep. 1, 2015, 9 pages.
Non-Final Office Action received for U.S. Appl. No. 13/615,107, mailed on Apr. 24, 2015, 9 pages.
Final Office Action received for U.S. Appl. No. 13/646,570, mailed on Dec. 23, 2014, 10 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 14/271,276, mailed on Feb. 25, 2015, 8 pages.
Final Office Action received for U.S. Appl. No. 14/271,342 mailed on Feb. 27, 2015, 7 pages.
Notice of Allowance received for U.S. Appl. No. 14/271,342, mailed on Mar. 13, 2015, 5 pages.
Office Action received for Canadian Patent Application No. 2,727,429, mailed on Apr. 14, 2015, 4 pages.
Office Action received for Canadian Patent Application No. 2,727,429, mailed on May 26, 2015, 1 page.
Decision to Grant received for Japanese Patent Application No. 2011513694, mailed on Oct. 7, 2014, 3 pages (official copy only). (See Communication under 37 CFR § 1.98(a) (3)).
Office Action Received for Japanese Patent Application No. 2014158517, mailed on May 19, 2015, 5 pages (2 pages of English Translation and 3 pages of Official Copy).
International Written Opinion received for PCT Patent Application No. PCT/US2012/023172, mailed on Sep. 28, 2012, 4 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Search Report received for PCT Patent Application No. PCT/US2009/047070, mailed on Jan. 19, 2010, 4 pages.
International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Search Report received for PCT Patent Application No. PCT/US2012/023172, mailed on Sep. 28, 2012, 3 pages.
International Search Report and Written Opinion received for PCT Patent Application No. PCT/US2013/031805 mailed on May 20, 2013, 13 pages.
Adams et al., U.S. Appl. No. 13/534,658, filed on Jun. 27, 2012, titled "Shock Wave Balloon Catheter with Multiple Shock Wave Sources", 35.

(56) References Cited

OTHER PUBLICATIONS

Adams et al., U.S. Appl. No. 13/777,807, filed Feb. 26, 2013, titled "Shock Wave Catheter System with ARC Preconditioning", 15 pages.
Hakala et al., U.S. Appl. No. 13/831,543, filed Mar. 14, 2013, titled "Low Profile Electrodes for an Angioplasty Shock Wave Catheter", 52 pages.
Non Final Office Action received for U.S. Appl. No. 12/482,995, mailed on Jul. 12, 2013, 11 pages.
Hakala et al., U.S. Appl. No. 13/615,107, filed Sep. 13, 2012, titled "Shockwave Catheter System with Energy Control", 38 pages.
Office Action received for Australian Patent Application No. 2009257368, issued on Jul. 31, 2013, 4 pages.
Extended European Search Report (includes Supplementary European Search Report and Search Opinion) received for European Patent Application No. 097636401, mailed on Oct. 10, 2013, 5 pages.
International Preliminary Report on Patentability received for PCT Patent Application No. PCT/US2012/023172, mailed on Aug. 15, 2013, 6 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/059533, mailed on Nov. 7, 2013, 14 pages.
Office Action received for Japanese Patent Application No. 2011-513694, mailed on Aug. 27, 2013, 6 pages.
Final Office Action received for U.S. Appl. No. 13/267,383, mailed on Oct. 25, 2013, 8 pages.
Final Office Action received for U.S. Appl. No. 12/482,995, mailed on Feb. 20, 2014, 11 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.
Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
International Search Report and Written Opinion received for PCT Patent Application No. PCT/US2013/055431, mailed on Nov. 12, 2013, 9 pages.
Advisory Action received for U.S. Appl. No. 13/267,383, mailed on Jan. 6, 2014, 4 pages.
Non-Final Office Action received for U.S. Appl. No. 12/501,619, mailed on Jan. 28, 2014, 10 pages.
Non-Final Office Action received for U.S. Appl. No. 13/049,199, mailed on Feb. 4, 2014, 8 pages.
Notice of Allowance received for U.S. Appl. No. 14/515,130, mailed on May 2, 2016, 8 pages.
Non Final Office Action received for U.S. Appl. No. 13/534,658, mailed on Mar. 11, 2016, 12 pages.
Advisory Action received for U.S. Appl. No. 13/615,107, mailed on Nov. 6, 2015, 3 pages.
Notice of Allowance received for U.S. Appl. No. 13/615,107, mailed on Dec. 31, 2015, 10 pages.
Extended European Search Report received for European Patent Application No. 13827971.6, mailed on Apr. 12, 2016, 8 pages.
Non Final Office Action received for U.S. Appl. No. 14/515,130, mailed on Jan. 14, 2016, 16 pages.

SHOCKWAVE CATHETER SYSTEM WITH ENERGY CONTROL

CROSS-REFERENCE TO RELATED APPLICATION

This application is a continuation-in-part of U.S. application Ser. No. 13/615,107 filed on Sep. 13, 2012 (pending), which application is incorporated herein by reference in its entirety for all purposes.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the opening in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

Recently, a new system and method has been contemplated for breaking up calcium deposits in, for example, arteries and veins. Such a system is described, for example in U.S. Patent Publication No. 2009/0312768, Published Dec. 17, 2009. Embodiments described therein include a catheter having balloon, such as an angioplasty balloon, at the distal end thereof arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue.

Each high voltage pulse causes an arc to form across the electrodes. The arc in turn causes a steam bubble to form. Each steam bubble has the potential of producing two shock waves, a leading edge shock wave as a result of bubble expansion and a trailing edge shock wave as a result of bubble collapse. The trailing edge shock waves exhibit highly variable energy levels and generally, much greater energy levels than the leading edge shock waves. The energy levels of the trailing edge shock waves are substantially dependent on the uniformity of the bubble collapse. The uniform collapse of spherical bubbles to a point appears to create the highest shock wave energies. Unfortunately, spherical bubble configuration requires a substantially larger space than is available in a balloon that must fit into a calcified vein or artery or even a ureter. In fact, the trailing edge shock wave can be substantially eliminated by confining the bubble to an irregular shape. As a result, for angioplasty or other cardiac and non-cardiac applications of shock waves, the trailing edge shock wave cannot be reliably relied upon to produce consistent results.

However, the leading edge shock waves formed by bubble expansion are a different matter. While exhibiting generally lower energies, they are more consistent in energy level. As a result, leading edge shock waves are good candidates for use in medical procedures such, for example, angioplasty or valvuloplasty.

Another consideration is the amount of energy represented by the high voltage applied to the electrodes. Each high voltage pulse removes a portion of the electrode material. Since the size of the electrodes must be small in order to fit into the calcified vein or artery, they are only capable of sustaining a limited numbers of high voltage pulses sufficient to form the shock wave resulting electrical arc.

Also, it has been learned that to sustain a leading edge shock wave, it is not necessary to sustain the high voltage throughout the shock wave. Sustaining the high voltage beyond some point after the initial arc does not lead to shock waves of any greater intensity. Further, since the bubbles are formed of steam, the steam produces heat which can increase the temperature of adjacent soft tissue. Just a two degree Celsius elevation in temperature above body temperature can result in tissue damage.

A still further important aspect of prior art attempts to use shock waves from electrical arcs for therapeutic purposes is that from the time the high voltage is first applied to the electrodes to the time in which the arc occurs there is a dwell time (Td) that is highly variable from one high voltage application to the next. To account for the dwell times that are long, prior art strategies have relied upon high voltage applications where all high voltage pulse durations or pulse widths are of the same length and of a length sufficient to extend through the longest of the anticipated dwell times plus the associated arc and steam bubble. As a result, when the dwell times are shorter than the maximum, the high voltage application durations are longer than necessary and can unnecessarily extend the arc and the steam bubble well beyond a time required to produce a shock wave of maximum intensity. The result is wasted energy, extended electrode erosion, and unnecessary heating of the adjoining tissue.

Hence, there is a need in the art to be able to control the energy applied to the electrodes of an electrical arc shock wave generator. More particularly, there is a need to control the applied energy to assure appropriate bubble and shock wave formation while at the same time conserving electrode material and assuring tissue safety. The present invention addresses these and other issues.

SUMMARY OF THE INVENTION

In one embodiment, a system includes a catheter including an elongated carrier, a balloon about the carrier in sealed relation thereto, the balloon being arranged to receive a fluid therein that inflates the balloon, and first and second electrodes within the balloon arranged to carry a voltage thereacross including an initial high electrical voltage at an initial low current. The initial high electrical voltage causes an electrical arc to form across the first and second electrodes within the balloon. The electrical arc causes a gas bubble within the liquid, a high current to flow through the first and second electrodes, a decrease in the initial high electrical voltage, and a mechanical shock wave within the balloon. The system further includes a power source that provides the first and second electrodes with a drive voltage that creates the initial high electrical voltage at the initial current and that terminates the drive voltage in response to the decrease in the initial high electrical voltage.

The power source may include a voltage sensor that senses the voltage across the first and second electrodes. The voltage sensor is arranged to cause the power source to terminate the drive voltage when the voltage across the first and second electrodes decreases by more than a predetermined amount of voltage within less than a predetermined amount of time.

The predetermined amount of voltage may be on the order of one-hundred volts and the predetermined time may be on the order of about 0.1 microseconds. Alternatively, the predetermined amount of voltage may be on the order of five-hundred volts and the predetermined time may be on the order of about 0.5 microseconds.

The system may further include a temperature sensor within the balloon that senses temperature of the fluid within the balloon, and the power source may be further responsive to the temperature sensor. The temperature sensor may cause the power source to decrease energy applied to the first and second electrodes responsive to the temperature of the fluid within the balloon increasing to control the temperature of the fluid.

The temperature sensor may be arranged to cause the power source to decrease energy applied to the first and second electrodes responsive to the temperature of the fluid within the balloon increasing to above two degrees Celsius above ambient temperature.

The balloon may be a dilation balloon. The dilation balloon is preferably an angioplasty balloon.

The system may further include a timer that times a delay time in response to the decrease in the initial high electrical voltage and the power source may be arranged to terminate the drive voltage after the delay time is timed.

The power source may include a voltage sensor that senses voltage across the first and second electrodes and the voltage sensor may be arranged to cause the timer to time the delay time when the voltage across the first and second electrodes decreases by more than a predetermined amount of voltage within less than a predetermined amount of time. The predetermined amount of voltage may be on the order of one-hundred volts and the predetermined time is on the order of about 0.1 microseconds. Alternatively, the predetermined amount of voltage may be on the order of five-hundred volts and the predetermined time is on the order of about 0.5 microseconds.

In another embodiment, a system includes a catheter including an elongated carrier, the carrier having a guide wire lumen, a balloon having an inner surface about the carrier in sealed relation thereto, the balloon forming with the carrier, a channel arranged to receive a fluid that inflates the balloon, and first and second electrodes within the balloon between the carrier and the inner surface of the balloon. The first and second electrodes within the balloon are arranged to carry a voltage there-across including an initial high electrical voltage at an initial low current. The initial high electrical voltage causes an electrical arc to form across the first and second electrodes within the balloon. The electrical arc causes a gas bubble within the liquid, a high current to flow through the first and second electrodes, a decrease in the initial high electrical voltage, and a mechanical shock wave within the balloon. The system further includes a power source that provides the first and second electrodes with a drive voltage that creates the initial high electrical voltage at the initial current and that terminates the drive voltage in response to the decrease in the initial high electrical voltage.

In a further embodiment, a method includes the steps of: providing a catheter including an elongated carrier, a balloon about the carrier in sealed relation thereto, the balloon being arranged to receive a fluid therein that inflates the balloon, and first and second electrodes within the balloon and introducing the fluid into the balloon to inflate the balloon. The method further includes the steps of applying a drive voltage across the first and second electrodes to form an electrical arc across the first and second electrodes, sensing voltage across the first and second electrodes and varying the application of the drive voltage across the first and second electrodes in response to sensed voltage across the first and second electrodes after the electrical arc is formed across the first and second electrodes.

The varying step may include terminating the application of the drive voltage across the first and second electrodes.

The application of the drive voltage may be terminated when the voltage across the first and second electrodes decreases by more than a predetermined amount of voltage within less than a predetermined amount of time. The predetermined amount of voltage may be on the order of one-hundred volts and the predetermined time is on the order of 0.1 microseconds. Alternatively, the predetermined amount of voltage may be on the order of five-hundred volts and the predetermined time is on the order of about 0.5 microseconds.

The method may further include the step of sensing temperature of the fluid within the balloon, and the varying step may include varying the drive voltage across the first and second electrodes in response to sensed temperature of the fluid. The varying step may include decreasing energy applied to the first and second electrodes responsive to the temperature of the fluid within the balloon increasing to control the temperature of the fluid. The energy applied to the first and second electrodes may be decreased responsive to the temperature of the fluid within the balloon increasing to above two degrees Celsius above ambient temperature.

The method may further include the step of timing a delay time when the voltage across the first and second electrodes decreases by more than a predetermined amount of voltage within less than a predetermined amount of time.

The predetermined amount of voltage may be on the order of one-hundred volts and the predetermined time is on the order of about 0.1 microseconds. The predetermined amount of voltage may alternatively be on the order of five-hundred volts and the predetermined time is on the order of about 0.5 microseconds.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
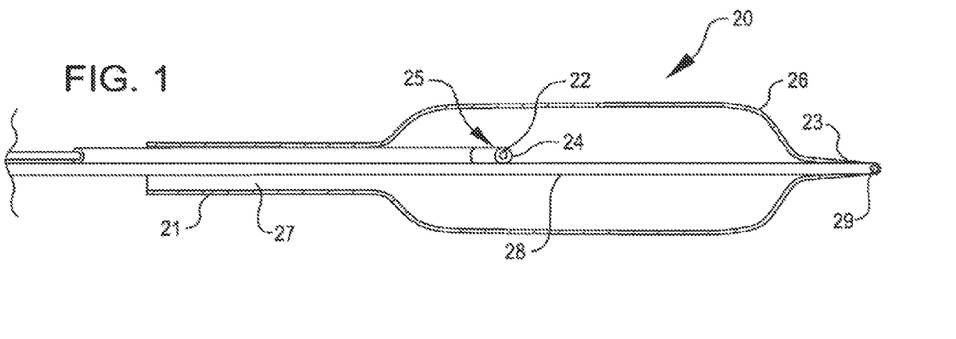
FIG. 1 is a simplified side view of an angioplasty balloon catheter of the type that may utilize various embodiments of the invention to advantage.

FIG. 1 is a simplified side view of an angioplasty balloon catheter 20 of the type that may utilize various embodiments of the invention to advantage. The catheter 20 includes an elongated carrier, such as a hollow sheath 21, a dilating balloon 26 formed about the sheath 21 in sealed relation thereto and a guide wire member 28 to which the balloon is sealed at a seal 23. The guide wire member has a longitudinal lumen 29 through which a guide wire (not shown) may be received for directing the catheter 20 to a desired location within a vein or artery, for example.

The sheath 21 forms with the guide wire member 28 a channel 27 through which fluid, such as saline, may be admitted into the balloon to inflate the balloon. The channel 27 further permits the balloon 26 to be provided with an electrode pair 25 including electrodes 22 and 24 within the fluid filled balloon 26.

Figure 2:
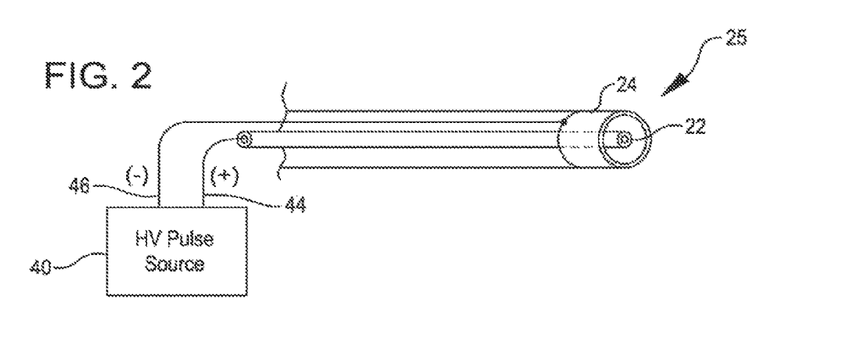
FIG. 2 is a simplified side view of an electrode structure that may be employed in the catheter of FIG. 1 coupled to a source of high voltage pulses according to one embodiment of the invention.

As may be seen in FIG. 2, the electrodes 22 and 24 are attached to a source 40 of high voltage pulses. As may be seen in FIG. 3, the electrodes 22 and 24 are coaxially disposed with electrode 22 being a center electrode and electrode 24 being a ring shaped electrode about electrode 22. The center electrode 22 is coupled to a positive terminal 44 of source 40 and the ring electrode 24 is coupled to a negative terminal 46 of the source 40. The electrodes 22 and 24 are formed of metal, such as stainless steel, and are maintained a controlled distance apart to allow a reproducible arc to form for a given applied voltage and current.

Figure 3:
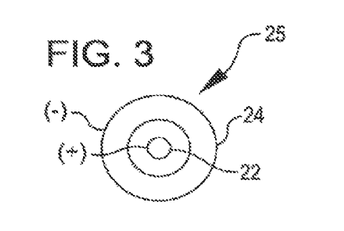
FIG. 3 is a front plan view of the electrode structure of FIG. 2.

The electrical arcs between electrodes 22 and 24 in the fluid are used to generate shock waves in the fluid. Each pulse of high voltage applied to the electrodes 22 and 24 forms an arc across the electrodes. The voltage pulses may have amplitudes as low as 500 volts, but preferably, the voltage amplitudes are in the range of 1000 volts to 10,000 volts The balloon 26 may be filled with water or saline in order to gently fix the balloon in the walls of the artery or vein, for example, in direct proximity with the calcified lesion. The fluid may also contain an x-ray contrast to permit fluoroscopic viewing of the catheter during use. Once the catheter 20 is positioned with the guide wire (not shown), the physician or operator can start applying the high voltage pulses to the electrodes to form the shock waves that crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 4:
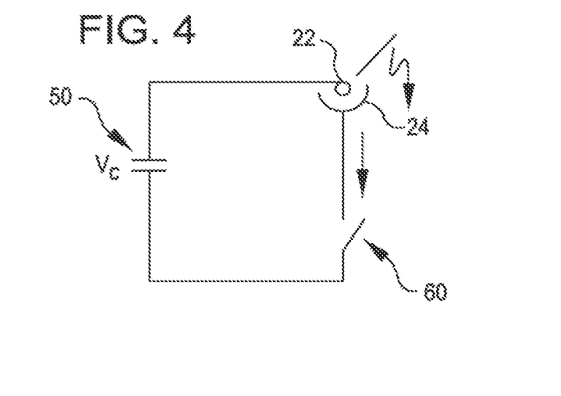
FIG. 4 is a simplified equivalent circuit diagram of a system according to an embodiment of the invention.

FIG. 4 is a simplified equivalent circuit diagram of a system according to an embodiment of the invention. Here it may be seen that a capacitance stores a high voltage. When a switch 60 is closed, the voltage drop across the electrodes 22 and 24 begins to quickly rise at an initially low current level. After a dwell time, when the voltage across the electrodes reaches the breakdown voltage of the fluid between the electrodes, an electrical arc occurs across the electrodes. The arc causes a steam bubble to form between the electrodes and a relatively high current to flow through the electrodes. The expansion of the bubble forms a first or leading edge shock wave. After a time, the steam bubble cools and condenses causing the bubble to collapse. The collapsing bubble has the potential for forming a second or trailing edge shock wave. As previously mentioned, the trailing edge shock wave is relatively unreliable exhibiting inconsistent intensities from shock wave to shock wave. Hence, it is the leading edge shock wave that holds the most promise for reliable therapy.

It has been found that effective shock wave intensity may be accomplished without holding the high voltage pulses on during the entire extent of their corresponding steam bubbles. Moreover, terminating the application of the high voltage before steam bubble collapse can serve to preserve electrode material, permitting a pair of electrodes to last for an increased number of applied high voltage pulses. Still further, as will be seen subsequently, early termination of the high voltage can also be used to advantage in controlling the temperature within the balloon fluid.

Figure 5:
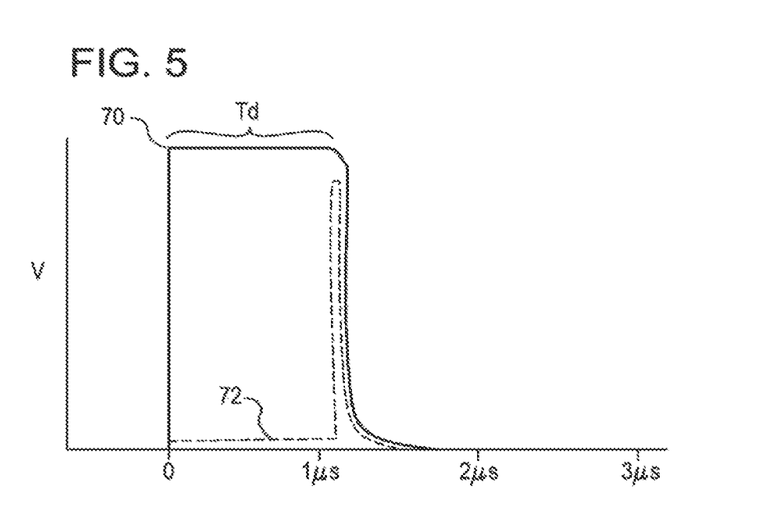
FIG. 5 is a graph illustrating a high voltage pulse applied to a pair of electrical arc shock wave producing electrodes and the resulting current flow through the electrodes in accordance with an embodiment of the invention.

FIG. 5 is a graph illustrating a high voltage pulse applied to a pair of electrical arc shock wave producing electrodes and the resulting current flow through the electrodes in accordance with an embodiment of the invention. When the switch 60 (FIG. 4) is first closed, the voltage across the electrodes quickly rises to a level 70. During this time, as shown by dashed lines 72, the current through the electrodes is relatively low. After a dwell time (Td), the arc occurs between the electrodes. At this time the steam bubble begins to form and a high current begins to flow through the electrodes. In accordance with embodiments of the invention, responsive to the current through the electrodes, the application of the high voltage is terminated. This conserves energy applied to the electrodes, causing the electrodes to remain useful for a greater number of pulses than otherwise would be the case if the high voltage were applied longer or sustained throughout the bubble existence. The advantages of controlling the applied energy in this manner are obtained without adversely affecting the intensity of the leading edge shock waves produced.

Figure 6:
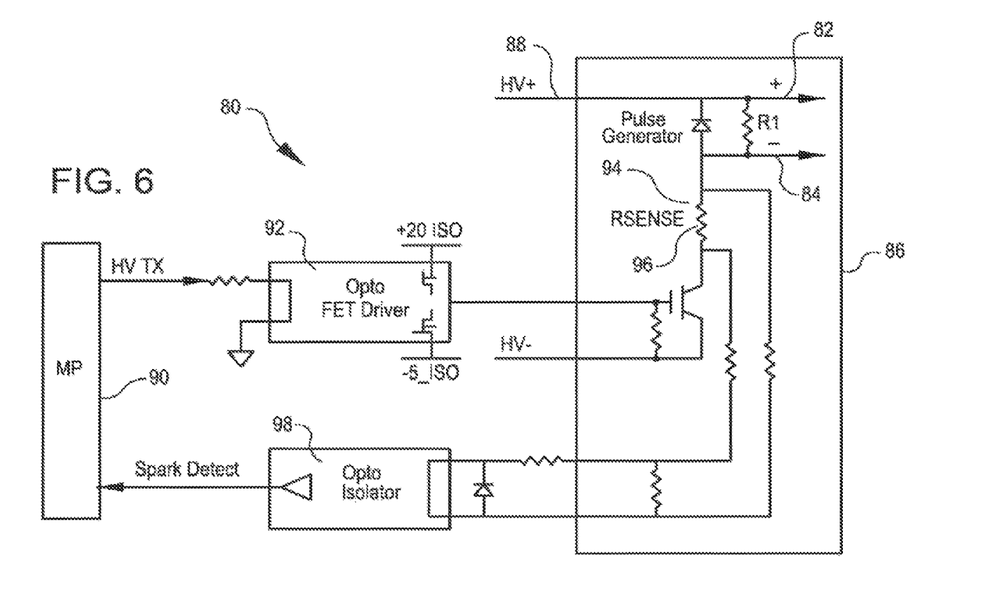
FIG. 6 is a schematic diagram of a power source for use in an angioplasty electrical arc shock wave angioplasty catheter according to an embodiment of the invention.

FIG. 6 is a schematic diagram of a power source 80 for use in an electrical arc shock wave angioplasty catheter according to an embodiment of the invention. The power source 80 has an output terminal 82 that may be coupled to electrode 22 of FIG. 1 and an output terminal 84 that may be coupled to electrode 24 of FIG. 1. A switch circuit 86 selectively applies a high voltage on line 88 across the electrodes. A microprocessor 90, or other similar control circuitry, such as a gate array, controls the overall operation of the source 80. A Field Programmable Gate Array (FPGA) may also be substituted for the microprocessor in a manner known in the art. The microprocessor 90 is coupled to the switch 86 by an optical driver 92. The switch includes a current sensor 94 that includes a current sensing resistor 96 that generates a signal that is applied to an optical isolator 98 when the current flowing through the electrodes reaches a predetermined limit, such as, for example, fifty (50) amperes.

In operation, the microprocessor 90 through the optical driver 92, causes the switch 86 to apply the high voltage to the electrodes 22 and 24. The current sensed through resister 96 is monitored by the microprocessor 90 through the optical isolator 98. When the current flowing through the electrodes reaches a predetermined limit, as for example 50 amperes, the microprocessor 90 causes the application of the high voltage to be terminated. The forgoing occurs for each high voltage pulse applied to the electrodes 22 and 24. Each pulse creates a shock wave of consistent and useful intensity. Further, because the application of the high voltage is terminated early, the electrode material is preserved to lengthen the useful life of the electrodes.

Figure 7:
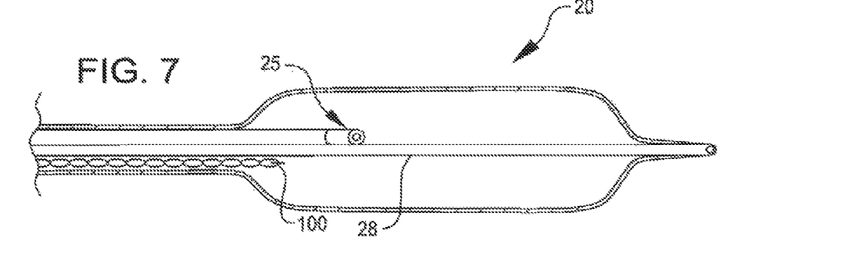
FIG. 7 is a side view of a dilating catheter with an electrical arc producing electrode structure and a temperature probe therein according to aspects of the invention.

FIG. 7 is a side view of a dilating catheter with an electrical arc producing electrode structure and a temperature probe therein according to aspects of the invention. The catheter 20 of FIG. 7 may be the same catheter as shown in FIG. 1. Here however, the catheter 20 further includes a temperature probe or sensor 100. The temperature sensor may be employed for sensing the temperature of the fluid within the balloon. Preferably, the temperature of the fluid within the balloon 26 should not be permitted to rise more than two degrees Celsius above the ambient body temperature. If this were to occur, soft tissue damage may result.

Figure 8:
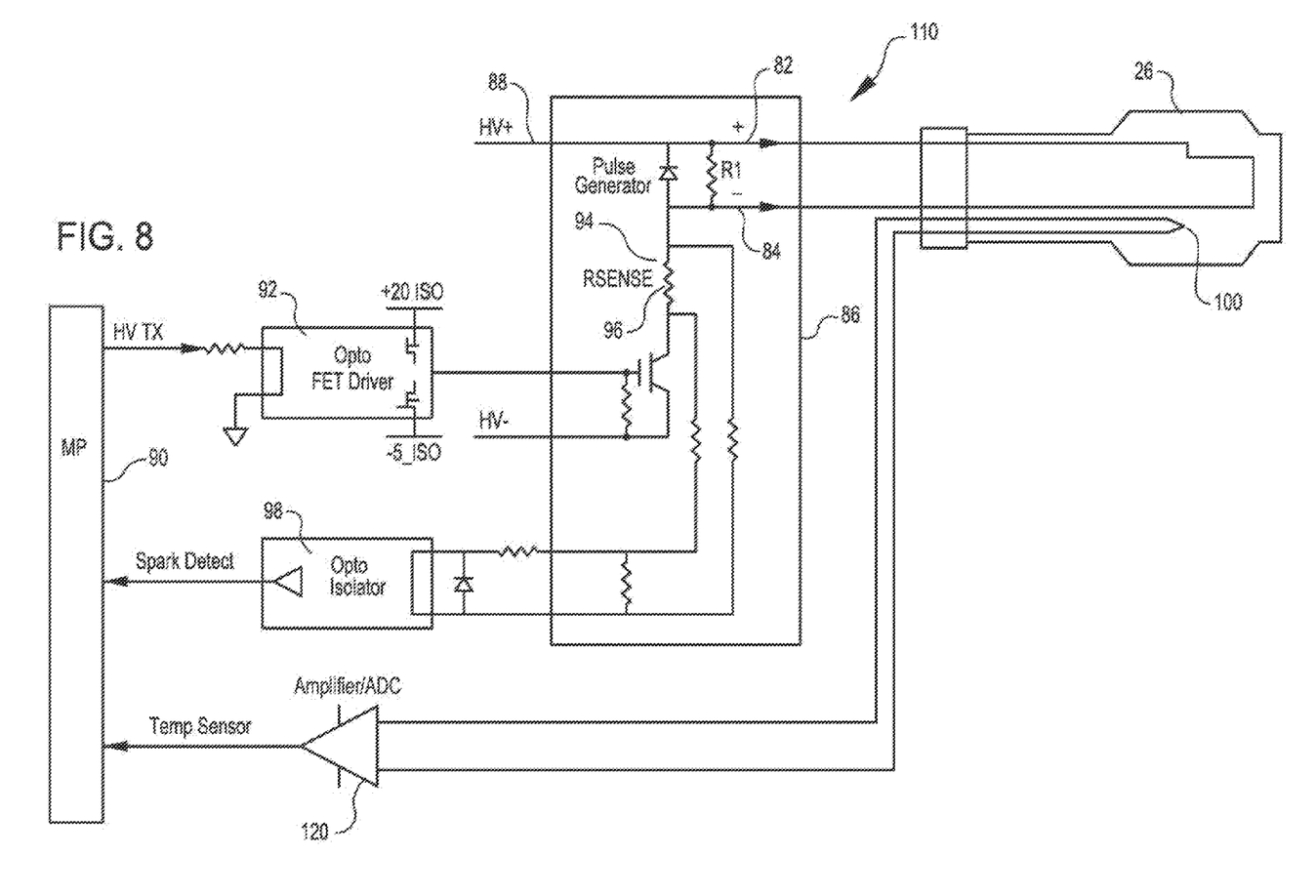
FIG. 8 is a schematic diagram of an angioplasty catheter system according to further embodiments of the invention.

FIG. 8 is a schematic diagram of an angioplasty catheter system 110 according to further embodiments of the invention which includes the catheter 20 and temperature probe 100. Here the system also includes the microprocessor 90, the switch 86, optical driver 92 and optical isolator 98. All of these elements may function as previously described. In addition, the temperature sensor 100 conveys a temperature signal through another optical isolator 120 indicative of the temperature of the fluid within the balloon 26. If the temperature within the balloon 26 rises to more than a certain temperature, for example to more than two degrees Celsius above ambient body temperature, the energy applied to the electrodes is decreased. This will decrease the size and duration of the steam bubbles produced by the electrodes to maintain the temperature of the fluid within the balloon to within safe limits. The microprocessor 90 may cause the switch 86 to decrease the pulse amplitude of the applied high voltage pulses or the pulse rate of the applied high voltage pulse. It could alternatively temporarily terminate the application of the pulses.

Figure 9:
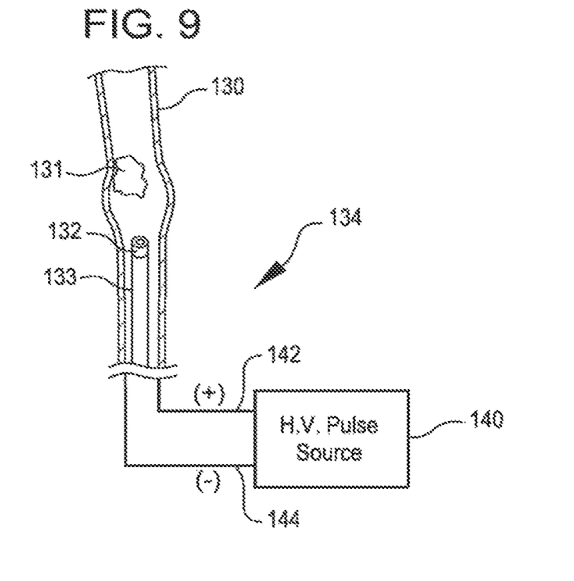
FIG. 9 is a simplified side view, partly in section, of a further embodiment wherein a balloon is not required.

FIG. 9 is a simplified side view, partly in section, of a further embodiment wherein a balloon is not required. In this embodiment, a system 134, according to further aspects of the invention, is shown treating an obstruction, more particularly, a kidney stone 131. The system includes a catheter 133 that terminates at its distal end with an electrode pair 132 similar to electrode pair 25 of FIGS. 1 and 2. The system further includes a power source 140. The power source has a positive output terminal 142 and a negative output terminal 144. The center electrode of the electrode pair 132 may be coupled to the positive terminal 142 of source 140 and the ring electrode of the electrode pair 132 may be coupled to the negative terminal 144 of the source 140. The electrodes of the electrode pair 132 may be formed of metal, such as stainless steel, and are maintained a controlled distance apart to allow a reproducible arc to form for a given applied voltage and current.

The catheter 133 of system 134 is shown in a ureter 130. The ureter has a kidney stone 131 requiring treatment. According to this embodiment, voltage pulses are applied to the electrode pair 132 to produce leading edge shock waves as previously described. The shock waves propagate through the fluid within the ureter and impinge directly on the kidney stone 131. In a manner as previously described, the power source may be operated to maintain the energy applied to the electrode pair within limits to assure that the steam bubbles produced by the generated arcs do not harm the ureter. To that end, the amplitude or pulse rate of the applied voltages may be controlled. Hence, by controlling the energy of the current during the produced arc, such as by controlling the on time of the current, barotrauma to the ureter may be minimized even though a balloon is not employed as in previous embodiments. Of course, the system of FIG. 9 may be used in other body organs as well, such as the bile duct, for example.

Figure 10:
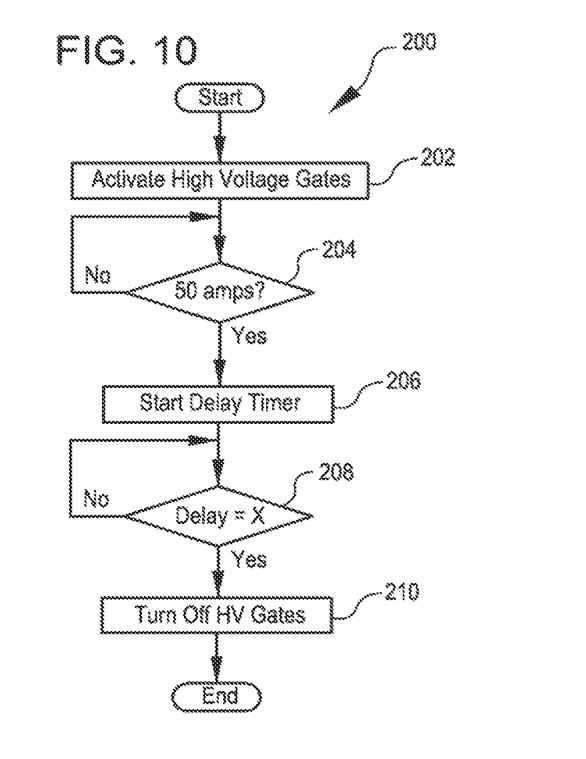
FIG. 10 is a flow diagram illustrating a further embodiment of the invention.

FIG. 10 is a flow diagram illustrating the process of a further embodiment of the invention. The embodiment of FIG. 10 takes into account the time it takes for a high voltage switch, such as switch 86 (FIG. 6), to turn off (the turn off time) and the rise time of the current flowing through the electrodes once the electrical arc starts. The current through the electrodes can eventually reach one-hundred amperes or more, at which point the maximum intensity shock wave will be formed. In order to permit the maximum current to be reached and to account for the turn off time of the switch 86, a delay is timed extending from when the current flowing through the electrodes is at a fixed threshold known to be below the maximum current, to the turn off time of the switch before the expected current maximum. For example, the current threshold may be fifty amperes. When the current through the electrodes equals fifty amperes, the delay timing is begun by the starting of a delay timer within the microprocessor 90. If the current is expected to be at a maximum 200 nanoseconds after the current reaches fifty amperes, and if it takes 100 nanoseconds for the high voltage switch to actually turn off after receiving a turn off signal, a delay of 100 nanoseconds should be timed from the 50 ampere sensing before a turn off signal is applied to the high voltage switch. Hence, a total time of 200 nanoseconds will pass after the current reaches 50 amperes and, as a result, will reach its maximum. As the current reaches its maximum, or shortly thereafter, the voltage applied to the electrodes will be terminated.

Referring now to the flow diagram 200 of FIG. 10, and also with reference to FIG. 6, the process begins with activity step 202 wherein the high voltage is applied to the output terminals 82 and 84 for application to the electrodes, for example, electrodes 22 and 24 (FIG. 1). At first, the current initially flowing through the electrodes is relatively low. However, after a dwell time, the applied high voltage causes an electrical arc to begin to form between the electrodes, the current through the electrodes is sensed, and the current rapidly rises. The current through the electrodes is sensed as previously described. At decision block 204, the microprocessor 90 determines if the sensed current has reached fifty amperes. When the current reaches fifty amperes, the process advances to activity block 206 where the timing of the aforementioned delay time (x) is started. Next, in decision block 208, it is determined when the delay time has been timed. In accordance with this embodiment, the delay time (x) may be 100 nanoseconds. When the delay time of 100 nanoseconds is timed, the process advances to activity block 210 wherein the process completes with a turn off signal being applied by the microprocessor 90 to the high voltage switch 86. The switch 86 will actually turn of a turn of time after the turn off signal is applied to the switch 86. Since it takes 100 nanoseconds for the switch to turn off and since 100 nanoseconds are timed before the turn off signal is applied to the switch, 200 nanoseconds form the 50 ampere current sensing will pass before the applied voltage to the electrodes is actually terminated. That provides sufficient time for the current to reach its maximum to generate the maximum intensity shock wave. The voltage application will terminated as the current reaches maximum, or shortly thereafter.

As a result of the foregoing, a maximum intensity shock wave is formed without wasting energy, without unduly eroding the electrodes, and without generating unnecessary heat. As may be appreciated, the delay timing may be employed to advantage in each of the embodiments disclosed herein including the embodiment of FIG. 9 which does not require a balloon.

Figure 11:
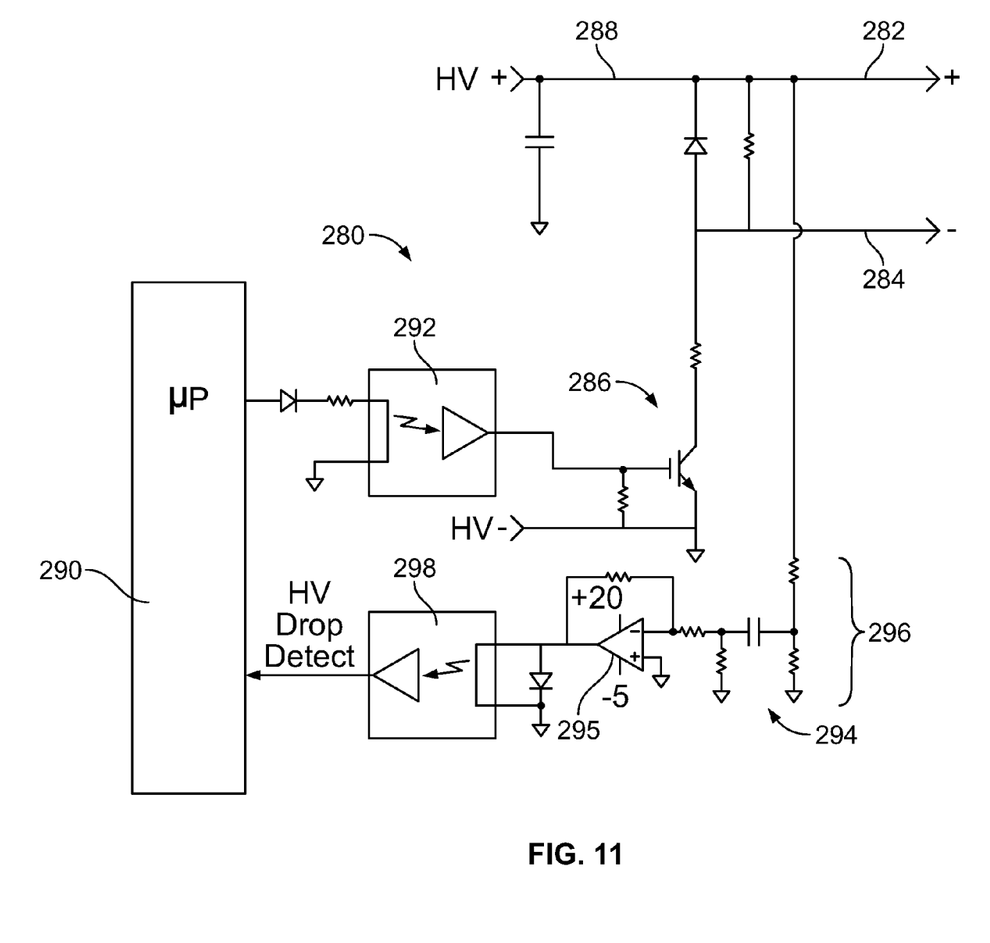
FIG. 11 is a schematic diagram of a power source for use in an angioplasty electrical arc shock wave angioplasty catheter according to a still further embodiment of the invention.

FIG. 11 is a schematic diagram of a power source 280 for use in an electrical arc shock wave angioplasty catheter according to a still further embodiment of the invention. Here the output switch of the power source is controlled in response to the voltage across the electrodes. More particularly, the power source provides a drive voltage that causes an initial high electrical voltage at an initial low current to be applied to the electrodes. The initial high electrical voltage causes an electrical arc to form across the first and second electrodes. The electrical arc causes a gas bubble within the liquid, a high current to flow through the first and second electrodes, a decrease in the initial high electrical voltage, and a mechanical shock wave within the balloon. The power source that provides the first and second electrodes with the drive voltage that creates the initial high electrical voltage at the initial current terminates the drive voltage in response to the decrease in the initial high electrical voltage. The power source may be arranged to terminate the drive voltage when the voltage across the electrodes decreases by more than a predetermined amount of voltage within less than a predetermined amount of time.

The power source 280 has an output terminal 282 that may be coupled to electrode 22 of FIG. 1 and an output terminal 284 that may be coupled to electrode 24 of FIG. 1. A switch circuit 286 selectively applies a high voltage on line 288 across the electrodes. A microprocessor 290, or other similar control circuitry, such as a gate array, controls the overall operation of the source 280. Again, a Field Programmable Gate Array (FPGA) may also be substituted for the microprocessor in a manner known in the art. The microprocessor 290 is coupled to the switch 286 by an optical driver 292. The switch includes a voltage sensor 294 that includes a voltage sensing resistive divider 296 that senses the output voltage. The divider is coupled to a capacitive coupled amplifier 295 that generates a signal that is applied to an optical isolator 298 when the voltage across the electrodes decreases by a predetermined amount within a predetermined amount of time to turn off the high voltage. For example, the voltage decrease required may be about 100 volts within about 0.1 microseconds or about 500 volts within about 0.5 microseconds.

In operation, the microprocessor 290 through the optical driver 292, causes the switch 286 to apply the high drive voltage (e.g., from about 1,500 V to about 4,000 V; about 3,000 V) to the electrodes 22 and 24. The output voltage sensed by the voltage sensing resistive divider 296 is monitored by the microprocessor 290 through the optical isolator 298. When the output voltage across the electrodes decreases by a predetermined amount within a predetermined amount of time as for example, by about 100 volts within about 0.1 microseconds or by about 500 volts within about 0.5 microseconds, the microprocessor 290 causes the application of the high voltage to be terminated. The forgoing occurs for each high voltage pulse applied to the electrodes 22 and 24. Each pulse creates a shock wave of consistent and useful intensity (i.e., such that the shock wave intensity is sufficient to crack a calcified lesion). Further, because the application of the high voltage is terminated early, the electrode material is preserved to lengthen the useful life of the electrodes.

Figure 12:
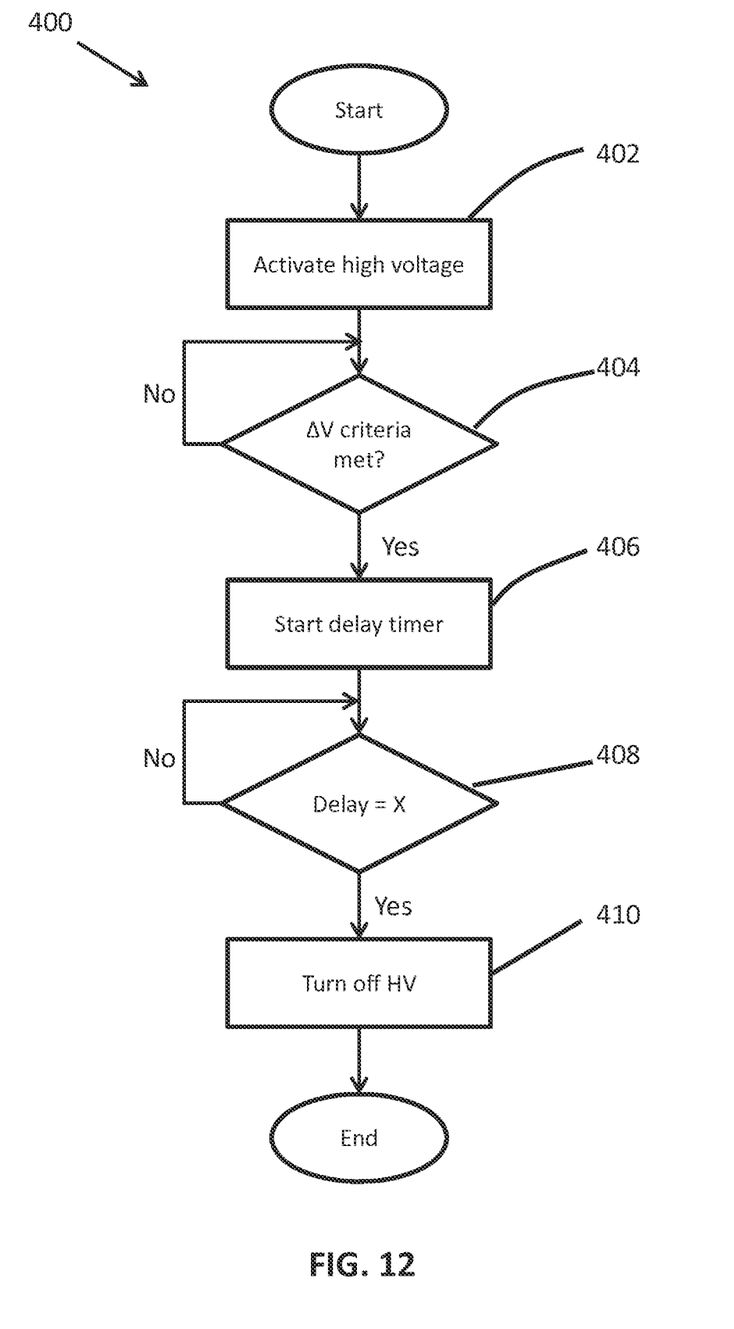
FIG. 12 is a flow diagram illustrating one manner in which the power source of FIG. 11 may operate in accordance with a still further embodiment.

FIG. 12 is a flow diagram illustrating a manner in which the power source of FIG. 11 may operate in accordance with a still further embodiment. The embodiment of FIG. 12 takes into account a fast response by the switch 286 to make sure that the output voltage is not terminated too early. This assures that a maximum output current and maximum intensity shock wave will be formed. In order to permit the maximum current to be reached a delay is timed extending from when the output voltage across the electrodes decreases by a predetermined amount within a predetermined amount of time. Again, for example, the predetermined voltage decrease and amount of time for the decrease may be about 100 volts within about 0.1 microseconds or about 500 volts within about 0.5 microseconds. The current threshold may be about fifty amperes. The delay timing is begun by the starting of a delay timer within the microprocessor 90. If the current is expected to be at a maximum 200 nanoseconds after the current reaches fifty amperes, and if it takes 100 nanoseconds for the high voltage switch to actually turn off after receiving a turn off signal, a delay of 100 nanoseconds should be timed from the 50 ampere sensing before a turn off signal is applied to the high voltage switch. Hence, a total time of 200 nanoseconds will pass after the current reaches 50 amperes and, as a result, will reach its maximum. As the current reaches its maximum, or shortly thereafter, the voltage applied to the electrodes will be terminated.

Referring now to the flow diagram 400 of FIG. 12, and also with reference to FIG. 11, the process begins with activity step 402 wherein a high drive voltage (e.g., from about 1,500 V to about 5,000 V, e.g., about 3,000 V) is applied to the output terminals 282 and 284 for application to the electrodes, for example, electrodes 22 and 24 (FIG. 1). At first, the voltage across the electrodes may be relatively high, e.g., from about 1,500 V to about 5,000 V, e.g., about 3,000 V. However, after a dwell time, the applied high voltage causes an electrical arc to begin to form between the electrodes. As the arc is formed, the voltage across the electrodes decreases rapidly. At decision block 404, the microprocessor 290 determines if the voltage decreases meets the predetermined voltage decrease and time criteria. When the criteria are met, the process advances to activity block 406 where the timing of the aforementioned delay time (x) is started. Next, in decision block 408, it is determined when the delay time has been timed. In accordance with this embodiment, the delay time (x) may be from about 0 ns to about 100 nanoseconds, e.g., 100 nanoseconds. When the delay time of 100 nanoseconds is timed, the process advances to activity block 410 wherein the process completes with a turn off signal being applied by the microprocessor 290 to the high voltage switch 286. The switch 286 will actually turn off a turn off time after the turn off signal is applied to the switch 286. If it takes 100 nanoseconds for the switch to turn off and since 100 nanoseconds are timed before the turn off signal is applied to the switch, 200 nanoseconds from the voltage decrease sensing will pass before the applied voltage to the electrodes is actually terminated. That provides sufficient time for the current to reach its maximum to generate the maximum intensity shock wave. The voltage application will be terminated as the current reaches maximum, or shortly thereafter.

While particular embodiments of the present invention have been shown and described, modifications may be made. It is therefore intended in the appended claims to cover all such changes and modifications which fall within the true spirit and scope of the invention as defined by those claims.

What is claimed is:

1. A system comprising:
    a catheter including an elongated carrier, a balloon about the carrier in sealed relation thereto, the balloon being arranged to receive a fluid therein that inflates the balloon, and first and second electrodes within the balloon arranged to carry a voltage there-across including an initial high electrical voltage at an initial low current, the initial high electrical voltage causing an electrical arc to form within the balloon, the electrical arc causing a gas bubble within the liquid, a high current to flow through the first and second electrodes, a decrease in the initial high electrical voltage, and a mechanical shock wave within the balloon; and
    a power source that provides the first and second electrodes with a drive voltage pulse that creates the initial high electrical voltage at the initial current and that terminates the drive voltage pulse in response to the decrease in the initial high electrical voltage.

2. The system of claim 1, wherein the power source includes a voltage sensor that senses the voltage across the first and second electrodes.

3. The system of claim 2, wherein the voltage sensor causes the power source to terminate the drive voltage pulse when the voltage across the first and second electrodes decreases by more than a predetermined amount of voltage within less than a predetermined amount of time.

4. The system of claim 3, wherein the predetermined amount of voltage is on the order of one-hundred volts and the predetermined time is on the order of about 0.1 microseconds.

5. The system of claim 3, wherein the predetermined amount of voltage is on the order of five-hundred volts and the predetermined time is on the order of about 0.5 microseconds.

6. The system of claim 1, further including a temperature sensor within the balloon that senses temperature of the fluid within the balloon, and wherein the power source is further responsive to the temperature sensor.

7. The system of claim 6, wherein the temperature sensor causes the power source to decrease energy applied to the first and second electrodes responsive to the temperature of the fluid within the balloon increasing to control the temperature of the fluid.

8. The system of claim 7, wherein the temperature sensor causes the power source to decrease energy applied to the first and second electrodes responsive to the temperature of the fluid within the balloon increasing to above two degrees Celsius above ambient temperature.

9. The system of claim 1, wherein the balloon is a dilation balloon.

10. The system of claim 1, wherein the dilation balloon is an angioplasty balloon.

11. The system of claim 1, further comprising a timer that times a delay time in response to the decrease in the initial high electrical voltage and wherein the power source terminates the drive voltage after the delay time is timed.

12. The system of claim 11, wherein the power source includes a voltage sensor that senses voltage across the first and second electrodes and wherein the voltage sensor causes the timer to time the delay time when the voltage across the first and second electrodes decreases by more than a predetermined amount of voltage within less than a predetermined amount of time.

13. The system of claim 12, wherein the predetermined amount of voltage is on the order of one-hundred volts and the predetermined time is on the order of about 0.1 microseconds.

14. The system of claim 12, wherein the predetermined amount of voltage is on the order of five-hundred volts and the predetermined time is on the order of about 0.5 microseconds.

15. A system comprising:
    a catheter including an elongated carrier, the carrier having a guide wire lumen, a balloon having an inner surface about the carrier in sealed relation thereto, a channel arranged to receive a fluid that inflates the balloon, and first and second electrodes, within the balloon between the carrier and the inner surface of the balloon, the first and second electrodes within the balloon being arranged to carry a voltage there-across including an initial high electrical voltage at an initial low current, the initial high electrical voltage causing an electrical arc to form within the balloon, the electrical arc causing a gas bubble within the liquid, a high current to flow through the first and second electrodes, a decrease in the initial high electrical voltage, and a mechanical shock wave within the balloon; and
    a power source that provides the first and second electrodes with a drive voltage pulse that creates the initial high electrical voltage at the initial current and that terminates the drive voltage pulse in response to the decrease in the initial high electrical voltage.

16. A balloon catheter for delivering shock waves to a calcified lesion comprising:
    an elongated carrier;
    a flexible balloon mounted on the elongate carrier, said balloon being fillable with a conductive fluid;
    a pair of electrodes on the elongated carrier within the balloon; and
    a power source coupled to the electrodes for supplying voltage pulses to the electrodes, each voltage pulse resulting in an initial high voltage across the electrodes that generates an arc in the fluid within the balloon and causes current to flow between the electrodes and producing a shock wave;
    wherein the power source includes a voltage sensor for detecting the voltage across the electrodes during each voltage pulse, and wherein when the voltage is reduced by a predetermined voltage value after the initial high voltage, the sensor generates a signal that causes the power source to terminate the voltage supplied to the electrodes for that pulse.

17. The balloon catheter of claim 16, wherein the power source is configured to terminate the voltage supplied to the electrodes when the initial high voltage drops by the predetermined value within a predetermined time interval.

18. The balloon catheter of claim 17, wherein the predetermined voltage value is about 100 V and the predetermined time interval is about 0.1 microseconds.

19. The balloon catheter of claim 17, wherein the predetermined voltage value is about 500 V and the predetermined time interval is about 0.5 microseconds.

20. The balloon catheter of claim 16, wherein the predetermined voltage value is from about 100 V to about 500 V.

21. The balloon catheter of claim 16, wherein the carrier has a guidewire lumen.

22. A balloon catheter for delivering shock waves to a calcified lesion comprising:
an elongated carrier;
a flexible balloon mounted on the elongate carrier, said balloon being fillable with a conductive fluid;
a pair of electrodes on the elongated carrier within the balloon; and
a power source coupled to the electrodes for supplying voltage pulses to the electrodes, each voltage pulse resulting in an initial high voltage across the electrodes that generates an arc in the balloon producing a shock wave, wherein the power source includes a voltage sensor configured to detect the voltage across the electrodes during each pulse;
wherein the power source is configured to terminate the supplied voltage pulse after the voltage across the electrodes for that pulse is reduced by a predetermined voltage value during a predetermined time interval.

23. The balloon catheter of claim 22, wherein the predetermined voltage value is about 100 V and the predetermined time interval is about 0.1 microseconds.

24. The balloon catheter of claim 22, wherein the predetermined voltage value is about 500 V and the predetermined time interval is about 0.5 microseconds.

25. The balloon catheter of claim 22, wherein the carrier has a guidewire lumen.

26. A catheter for delivering shock waves to a calcified lesion comprising:
an elongated carrier;
a pair of electrodes carried by the carrier, said electrodes being immersed in a conductive fluid; and
a power source with a circuit coupled to the electrodes for supplying voltage pulses to the electrodes, each voltage pulse generating an arc in the fluid and causing current to flow between the electrodes and producing a shock wave;
wherein the power source includes a voltage sensor for monitoring the voltage across the electrode pair and wherein when the voltage drops by a predetermined value during each voltage pulse, a signal is generated that causes the power source to terminate the voltage supplied to the electrodes for that pulse.

27. The catheter of claim 26, wherein the power source further includes a delay timer with a predetermined delay time, the delay timer being triggered in response to the generated signal and wherein the voltage supplied to the electrodes is terminated after the predetermined delay time has expired.

* * * * *